(12) United States Patent
Yoo et al.

(10) Patent No.: US 10,610,105 B2
(45) Date of Patent: Apr. 7, 2020

(54) OPTICAL PROBE INCLUDING WAVEFRONT MODULATOR FOR ENHANCING LATERAL RESOLUTION AND FOCAL DEPTH

(71) Applicant: IUCF-HYU (INDUSTRY-UNIVERSITY COOPERATION FOUNDATION HANYANG UNIVERSITY), Seongdong-Gu, Seoul (KR)

(72) Inventors: Hong Ki Yoo, Seoul (KR); Jun Young Kim, Seoul (KR); JingChao Xing, Seoul (KR)

(73) Assignee: IUCF-HYU (INDUSTRY-UNIVERSITY COOPERATION FOUNDATION HANYANG UNIVERSITY), Seongdong-Gu, Seoul (KR)

( * ) Notice: Subject to any disclaimer, the term of this patent is extended or adjusted under 35 U.S.C. 154(b) by 86 days.

(21) Appl. No.: 15/573,009

(22) PCT Filed: May 11, 2016

(86) PCT No.: PCT/KR2016/004916
§ 371 (c)(1),
(2) Date: Nov. 9, 2017

(87) PCT Pub. No.: WO2016/182333
PCT Pub. Date: Nov. 17, 2016

(65) Prior Publication Data
US 2018/0132727 A1    May 17, 2018

(30) Foreign Application Priority Data
May 12, 2015 (KR) .......................... 10-2015-0065980

(51) Int. Cl.
*A61B 5/00* (2006.01)
*A61B 1/06* (2006.01)
(Continued)

(52) U.S. Cl.
CPC .............. *A61B 5/0084* (2013.01); *A61B 1/00* (2013.01); *A61B 1/06* (2013.01); *A61B 1/07* (2013.01);
(Continued)

(58) Field of Classification Search
CPC ..... A61B 5/0084; A61B 5/02007; A61B 1/07; A61B 1/00; A61B 1/06; A61B 2562/0233;
(Continued)

(56) References Cited

U.S. PATENT DOCUMENTS

| 6,687,036 | B2 | 2/2004 | Riza |
| 7,072,045 | B2 * | 7/2006 | Chen .................... G01B 9/0201 356/479 |

(Continued)

FOREIGN PATENT DOCUMENTS

| JP | 2007-3829 A | 1/2007 |
| JP | 2007-530973 A | 11/2007 |

(Continued)

OTHER PUBLICATIONS

International Search Report for PCT/KR2016/004916, dated Aug. 17, 2016 (PCT/ISA/210).

*Primary Examiner* — Hwa Andrew Lee
(74) *Attorney, Agent, or Firm* — Sughrue Mion, PLLC

(57) ABSTRACT

An optical probe, according to one embodiment, comprises: an optical fiber into which light for irradiating an object is incident from a light source; a lens which focuses the light incident into the optical fiber; and a wavefront modulator on which a pattern is formed so that the wavefront of the light
(Continued)

incident into the optical fiber can be modulated, wherein the optical fiber, the lens, and the wavefront modulator are arranged on the same axis, the light passing through the wavefront modulator can form a focus on the same axis, and the resolution or focal depth of the light can be adjusted through a pattern design formed on the wavefront modulator.

8 Claims, 9 Drawing Sheets

(51) Int. Cl.
    *A61B 1/00*     (2006.01)
    *A61B 1/07*     (2006.01)
    *A61B 5/02*     (2006.01)
    *B29D 11/00*     (2006.01)
    *B29K 63/00*     (2006.01)

(52) U.S. Cl.
    CPC .... *A61B 5/02007* (2013.01); *B29D 11/00009* (2013.01); *A61B 2562/0233* (2013.01); *A61B 2562/12* (2013.01); *B29K 2063/00* (2013.01); *B29K 2883/00* (2013.01)

(58) Field of Classification Search
    CPC .......... A61B 2562/12; B29D 11/00009; B29K 2883/00; B29K 2063/00
    See application file for complete search history.

(56) References Cited

U.S. PATENT DOCUMENTS

| | | | |
|---|---|---|---|
| 9,642,531 B2* | 5/2017 | Tearney | ............... A61B 5/0066 |
| 2006/0109478 A1* | 5/2006 | Tearney | ............... A61B 5/0066 |
| | | | 356/479 |
| 2014/0218744 A1* | 8/2014 | De Boer | ............ G01B 9/02091 |
| | | | 356/479 |

FOREIGN PATENT DOCUMENTS

| | | |
|---|---|---|
| JP | 2015-29665 A | 2/2015 |
| JP | 2015-73846 A | 4/2015 |
| KR | 10-2012-0090007 A | 8/2012 |

* cited by examiner

[Fig. 1]
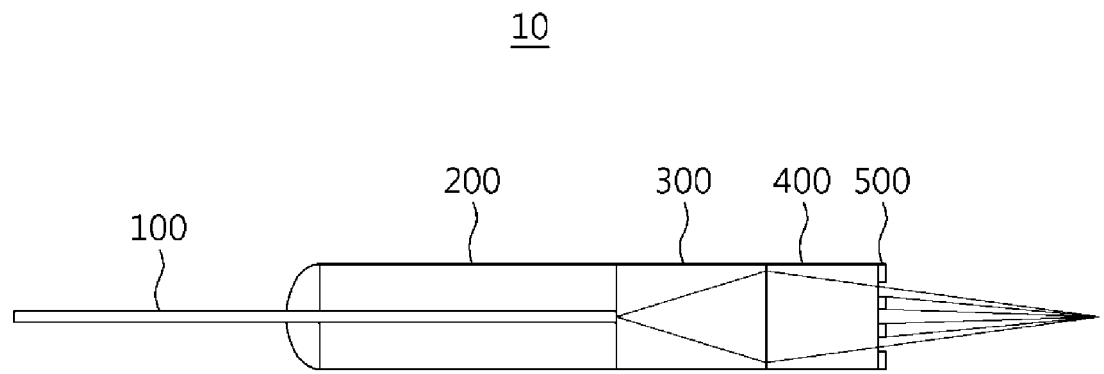
[Fig. 2a]
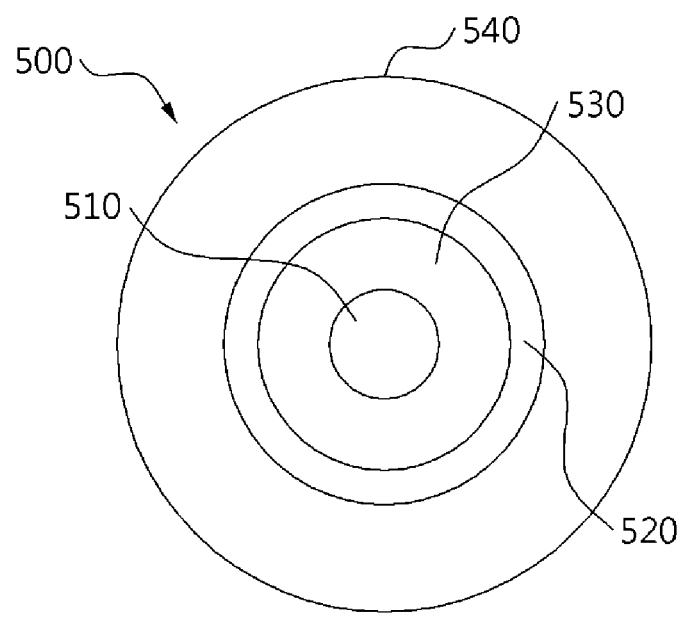

[Fig. 2b]
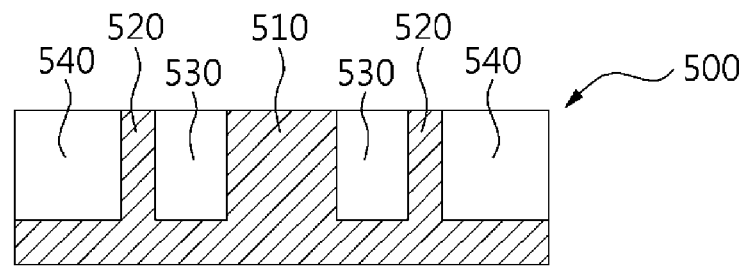
[Fig. 3a]
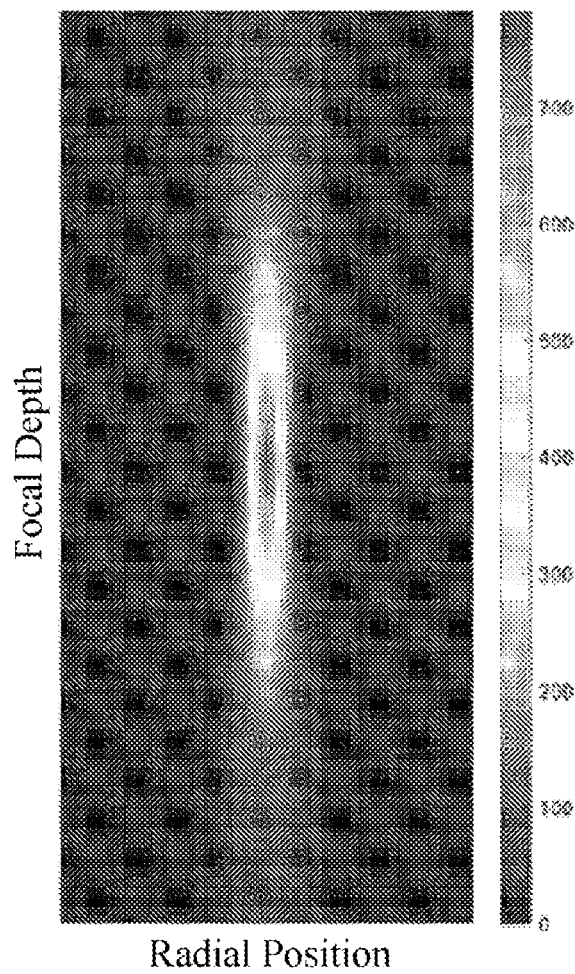

[Fig. 3b]
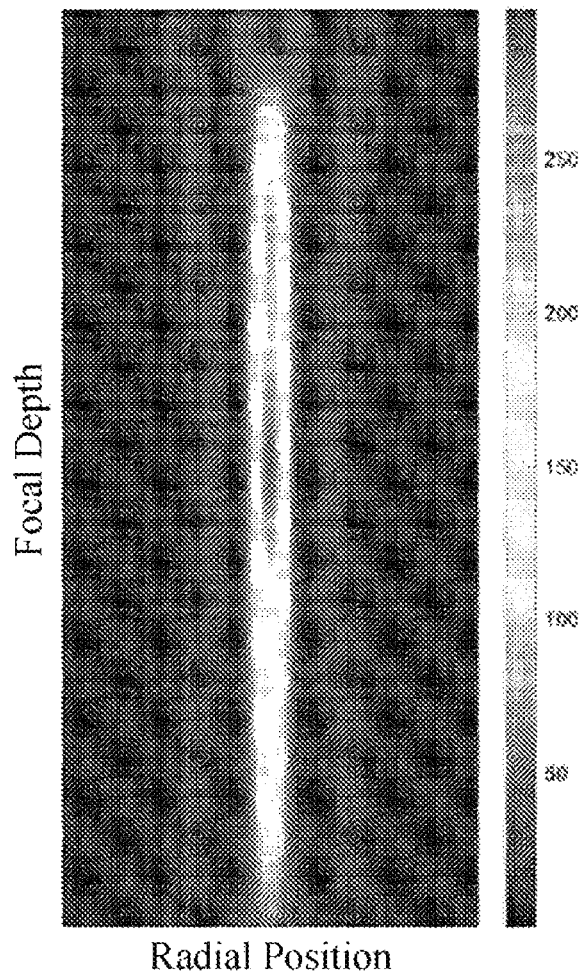
[Fig. 4]
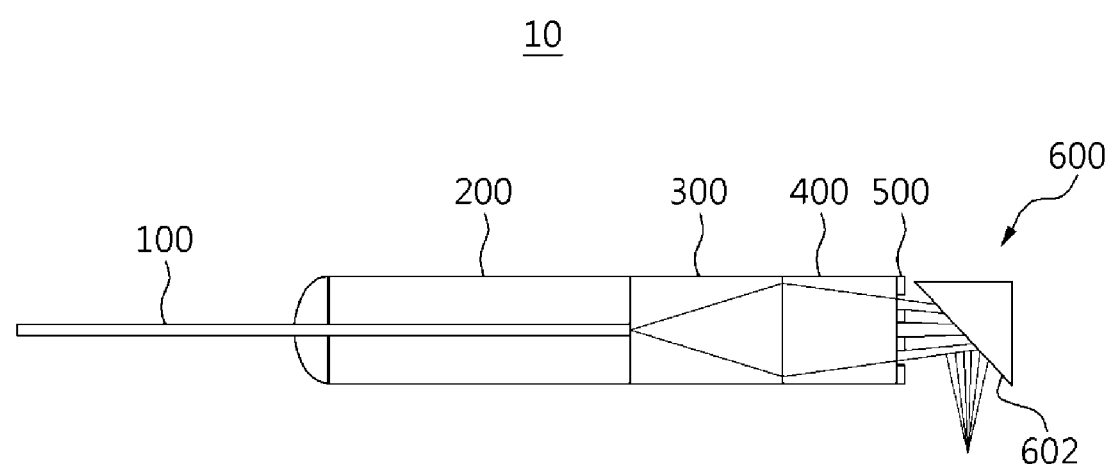

[Fig. 5]
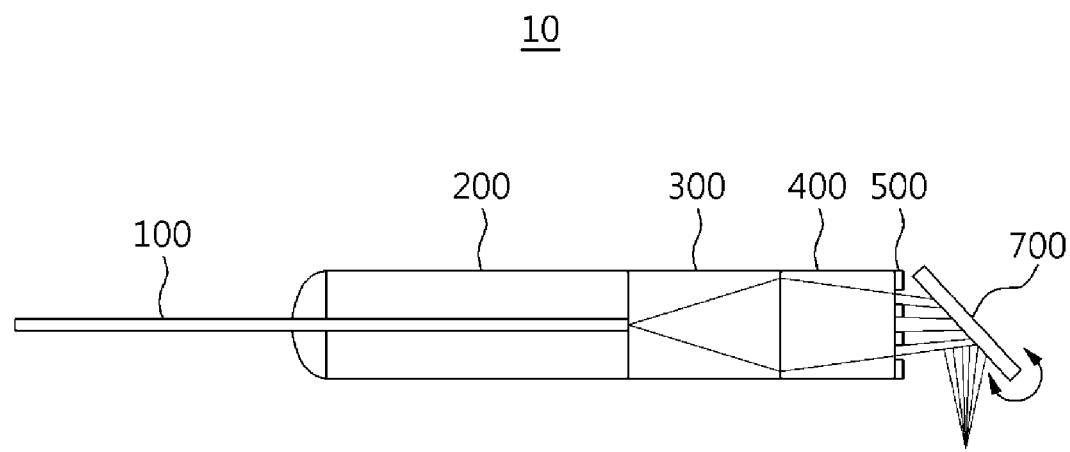
[Fig. 6]
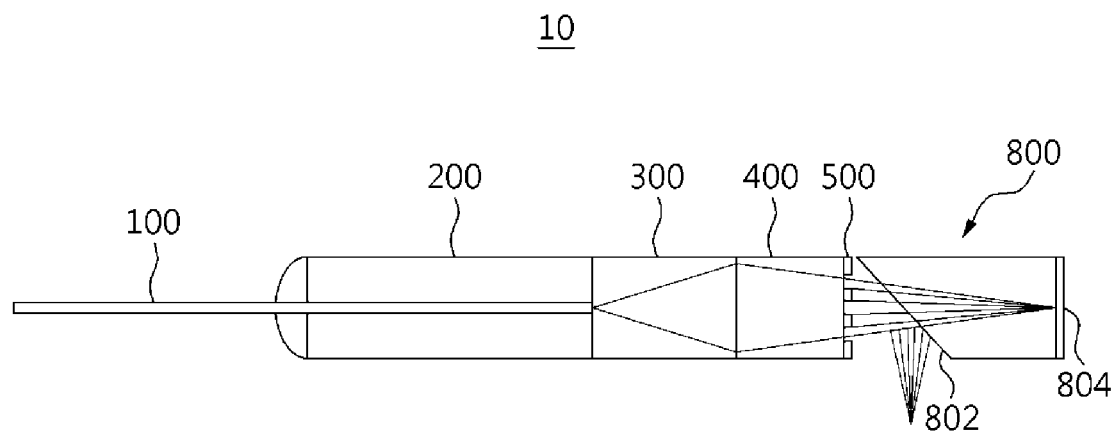

[Fig. 7]
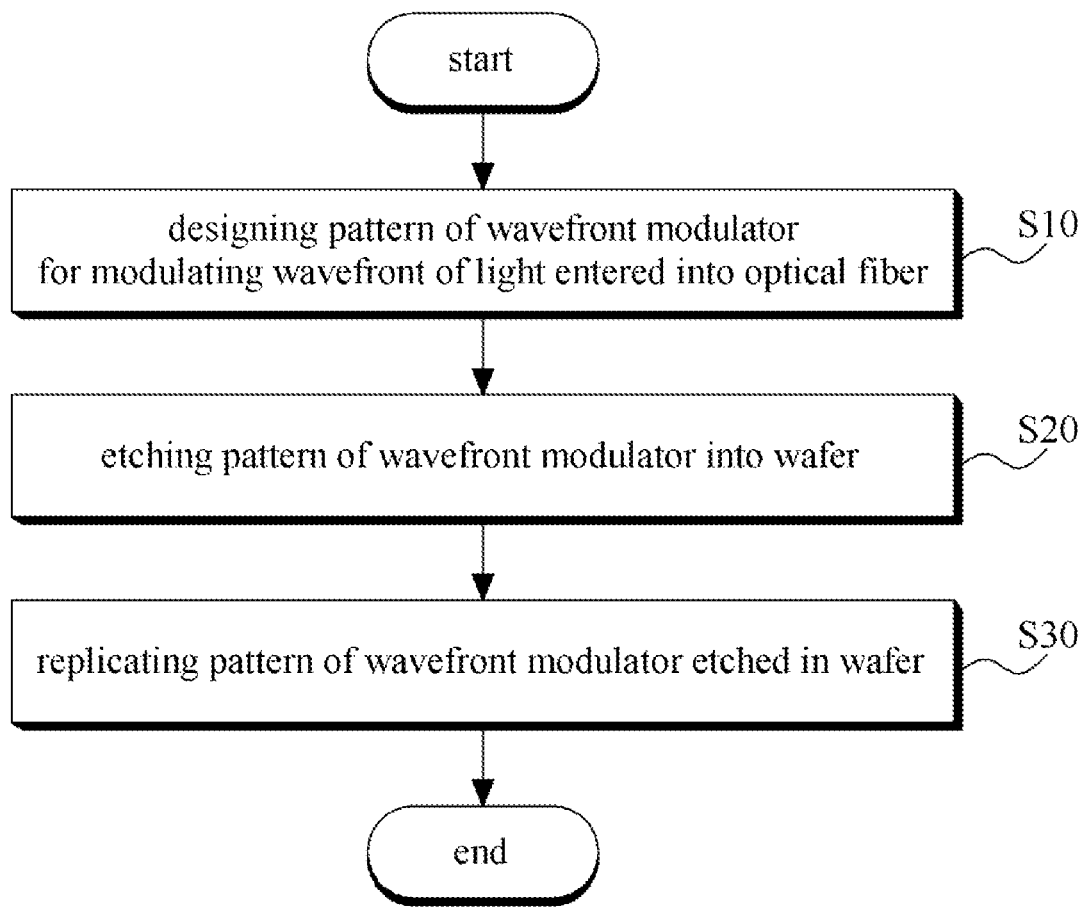

[Fig. 8a]
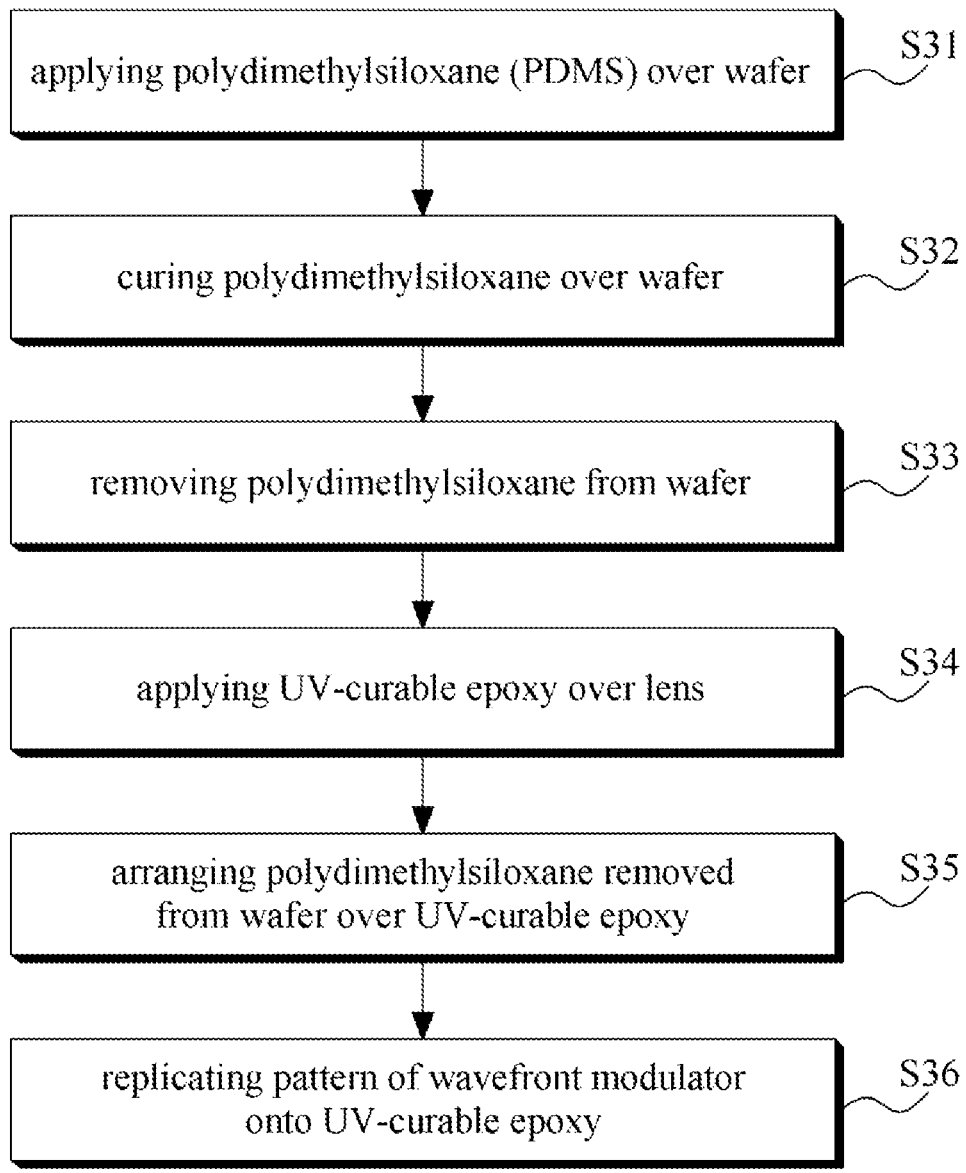

[Fig. 8b]
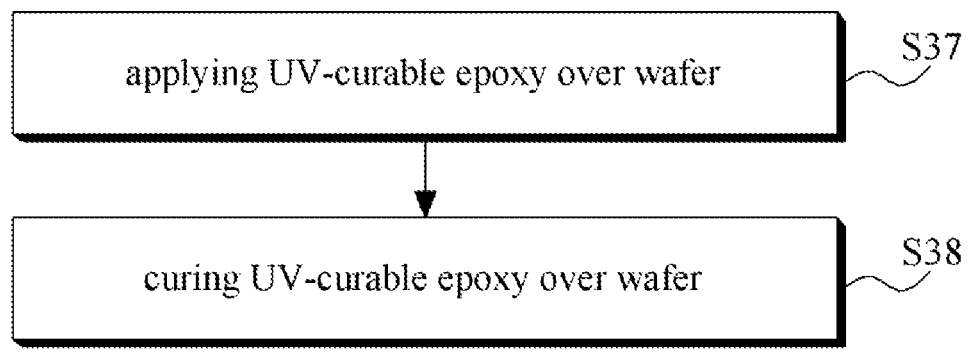
[Fig. 9a]
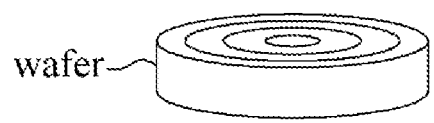
[Fig. 9b]
[Fig. 9c]
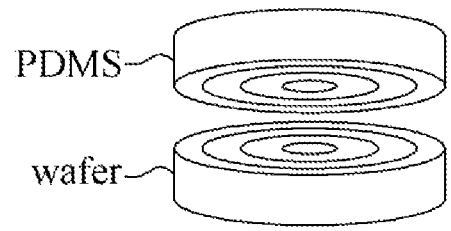

[Fig. 9d]
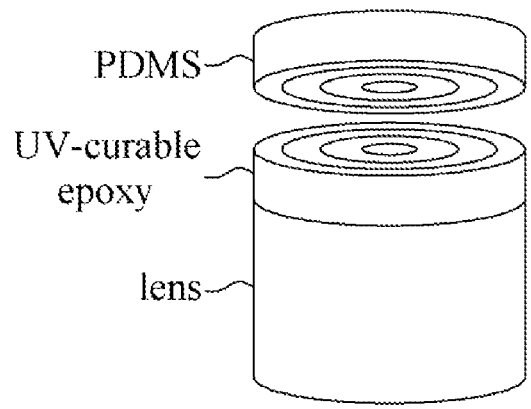
[Fig. 9e]
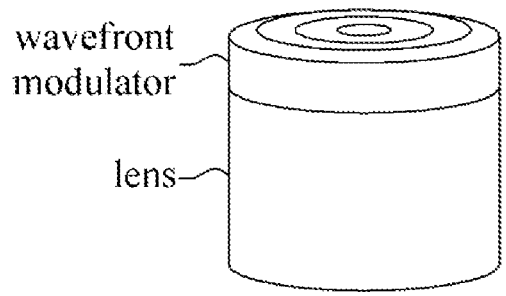
[Fig. 9f]
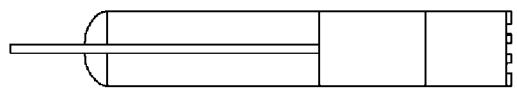

[Fig. 10a]
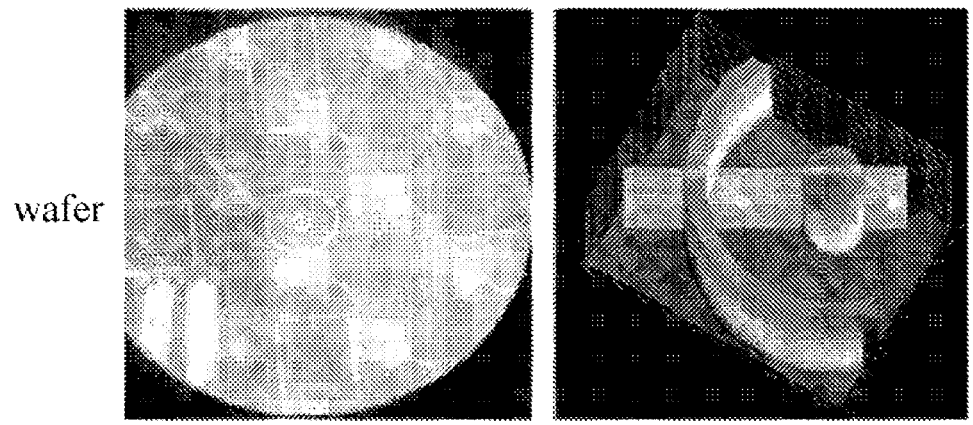
[Fig. 10b]
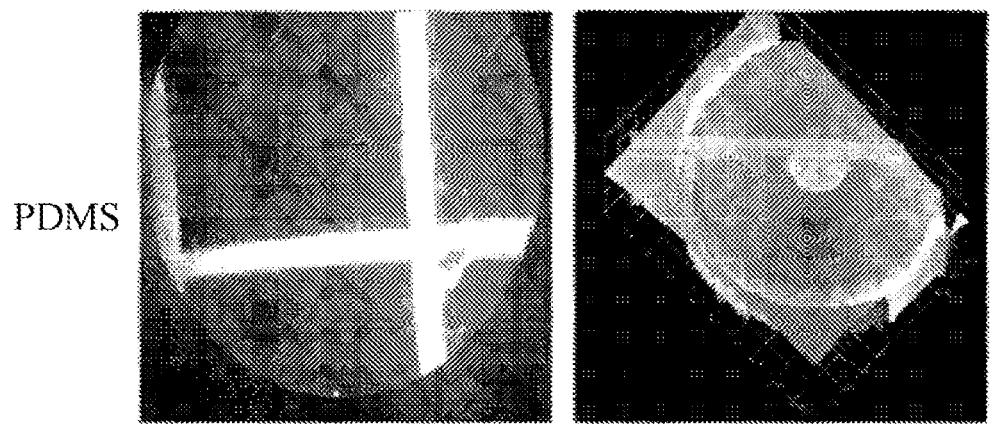
[Fig. 10c]
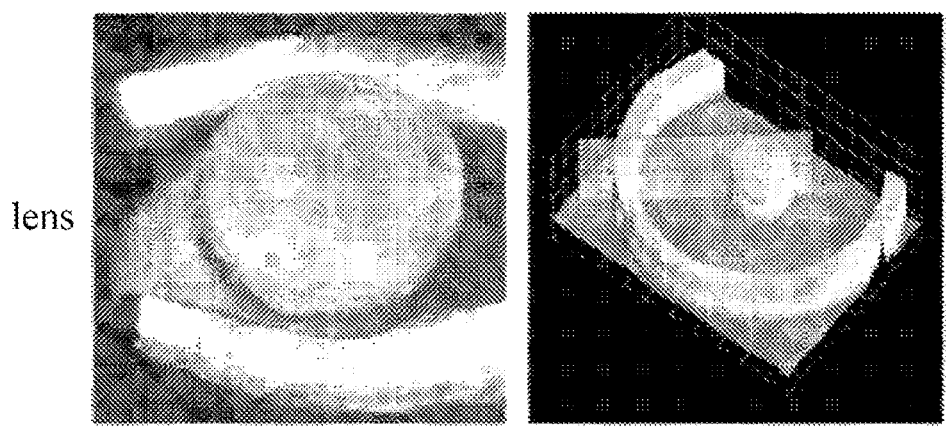

OPTICAL PROBE INCLUDING WAVEFRONT MODULATOR FOR ENHANCING LATERAL RESOLUTION AND FOCAL DEPTH

CROSS-REFERENCE TO RELATED APPLICATIONS

This application is a National Phase application of PCT International Application No. PCT/KR2016/004916, which was filed on May 11, 2016, and which claims priority from Korean Patent Application No. 10-2015-0065980 filed with the Korean Intellectual Property Office on May 12, 2015. The disclosures of the above patent applications are incorporated herein by reference in their entirety.

BACKGROUND

1. Technical Field

The present invention relates to an optical probe and a method for manufacturing the same, more particularly to an optical probe and method for manufacturing the optical probe that can improve lateral resolution and focal depth through an optimal design of the wavefront modulator.

2. Description of the Related Art

An endoscopic optical probe is generally being used in the diagnosis of cardiovascular diseases and digestive diseases. However, in optical coherence tomography, which is a technical field that uses the endoscopic optical probe, lateral resolution and focal depth are in a trade-off relationship.

Some examples of existing techniques aimed at overcoming this problem may include, among others, optical probes using axicon lenses or GRIN fibers and post-processing methods using software algorithms.

The optical probe using an axicon lens may have the optical probe manufactured with an axicon lens such that a Gaussian beam may be converted into a Bessel beam. Since a Bessel beam has a non-diffractive property, it can maintain a constant spot size over a large region, allowing an extension of the focal depth. However, a Bessel beam generated with this method may have large optical attenuation, making it difficult to use in imaging for biological tissues which requires high-sensitivity measurements.

The optical probe using a GRIN fiber may entail the use of a GRIN fiber, which is an optical fiber that has a gradient index at its core, where two GRIN fibers having different core sizes can be attached together. Here, the GRIN fiber having a smaller core size may serve as a phase filter, making it possible to extend the focal depth by about 1.5 times. However, the lengths of the GRIN fibers attached together have to be shorter than 200 μm and 30 μm, respectively, so that manufacturing this setup can be difficult.

A method of using a software algorithm may be a post-processing method that utilizes a software algorithm for extending the focal depth, where an algorithm based on the digital refocusing method, the inverse scattering approach, etc., may be employed. However, since such a method is a compensation method based on a post-processing operation and requires large amounts of computation and high complexity, it is difficult to achieve real time processing, and moreover, there is a risk of distortions caused by the influence of noise, etc.

For example, Korean Patent Application No. 2012-7026133 filed on Mar. 7, 2011, discloses "systems, methods and computer-accessible medium which provide microscopic images of at least one anatomical structure at a particular resolution," where multiple axicon lenses are configured to provide at least one electro-magnetic radiation.

As another example, Korean Patent Application No. 2010-0134640 filed on Dec. 24, 2010, discloses an "endoscopic spectral domain optical coherence tomography system based on optical coherent fiber bundle," where GRIN lenses are used in an optical fiber bundle to focus or collect an increased amount of light onto a sample end.

SUMMARY OF THE INVENTION

The objective of one embodiment is to provide an optical probe and a method for manufacturing the optical probe that can extend the measurement region along the depth direction while at the same time improving lateral resolution through an optimal design of the wavefront modulator.

The objective of one embodiment is to provide an optical probe and a method for manufacturing the optical probe in which the wavefront modulator is provided with a multiple number of annular regions so as to improve resolution or focal depth by changing the diameter sizes or height difference between the multiple annular regions.

The objective of one embodiment is to provide an optical probe and a method for manufacturing the optical probe that is capable of not only forward scanning but also circumferential scanning and 2-dimensional scanning by arranging a prism or a mirror in front of the optical probe.

The objective of one embodiment is to provide an optical probe and a method for manufacturing the optical probe that allow an easy alignment of the optical system and offer a solution to the problems of common noise and artifacts resulting from dispersion by using a common path optical probe.

The objective of one embodiment is to provide an optical probe and a method for manufacturing the optical probe where the optical probe can be manufactured via methods such as replica molding, precision molding, and direct molding, which are types of soft lithography, to allow easy manufacture and a smaller size for the optical probe.

The objective of one embodiment is to provide an optical probe and a method for manufacturing the optical probe that allows a precise diagnosis of lesions over a broader range compared to existing optical probes, to thus allow wide utility in diagnosing cardiovascular and digestive diseases, enable precise early diagnosis of arteriosclerosis, cancer in the digestive tract, etc., and aid in the research of pathogenic mechanisms by allowing the observation of reactions to drugs and treatments and of lesion developments, etc.

The objective of one embodiment is to provide an optical probe and a method for manufacturing the optical probe that can replace only the optical probe portion of an existing imaging device and thus can be applied in various fields.

An optical probe according to one embodiment, devised to achieve the objectives above, can include: an optical fiber configured to carry light entering from a light source for scanning a target; a lens configured to focus the light entered into the optical fiber; and a wavefront modulator in which a pattern is formed to modulate the wavefront of the light entered into the optical fiber, where the optical fiber, the lens, and the wavefront modulator can be arranged along a common axis, the light having passed through the wavefront modulator can form a focus on the common axis, and the resolution or focal depth of the light can be adjusted according to the design of the pattern formed in the wavefront modulator.

According to one aspect, the pattern formed in the wavefront modulator can include multiple of annular regions, where the annular regions can include a first annular region, a second annular region radially separated from the first annular region, and a third annular region arranged between the first annular region and the second annular region, and where the resolution or the focal depth of the light can be adjusted by a height difference or a diameter size of the first annular region, second annular region, and third annular region.

According to one aspect, the height difference between the multiple annular regions can be determined by the wavelength of the light and a difference in refractive index as:

$$d = \frac{\lambda}{2(n_1 - n_2)}$$

where d is the height difference between the plurality of annular regions, n1 is the refractive index of the first annular region, n2 is the refractive index of the third annular region, and λ is the wavelength of the light.

According to one aspect, the diameter sizes of the multiple annular regions can be determined by the type of the optical fiber and the size of the light entering the wavefront modulator.

According to one aspect, the first annular region can be positioned on the common axis, and the light having passed through the first annular region, the second annular region, and the third annular region can form a focus on the common axis.

According to one aspect, the wavefront modulator can be manufactured by etching the multiple annular regions in a wafer, replicating the multiple annular regions onto a polymer by applying the polymer over the wafer and curing the polymer, and adhering the replicated polymer onto the lens.

According to one aspect, a prism can further be included that is arranged in front of the wavefront modulator and separated from the wavefront modulator, where the light having passed through the wavefront modulator can be reflected off an inclined surface of the prism to form a focus on an axis perpendicular to the common axis.

According to one aspect, a mirror can further be included that is arranged in front of the wavefront modulator and separated from the wavefront modulator, where the point at which the light having passed through the wavefront modulator forms a focus can be controlled by controlling the inclination angle of the mirror.

According to one aspect, a splitter can further be included that is arranged in front of the wavefront modulator and separated from the wavefront modulator, where a portion of the light having passed through the wavefront modulator can be reflected off a surface of the splitter to form a focus on an axis perpendicular to the common axis, while a remaining portion of the light having passed through the wavefront modulator can pass through the surface of the splitter to form a focus on the common axis.

According to one aspect, one side of the splitter facing the wavefront modulator can be abraded to an angle of 40 to 50 degrees and applied with a splitter coating, and the other side of the splitter opposite the one side can be applied with a reflective coating.

According to one aspect, a spacer can further be included that is configured to diffuse light entered into the optical fiber, where the light entered into the optical fiber can be diffused to correspond to a diameter of the spacer.

A method for manufacturing an optical probe according to one embodiment, devised to achieve the objectives above, can include: designing a pattern of a wavefront modulator for modulating a wavefront of light entering an optical fiber; etching the pattern of the wavefront modulator in a wafer; and replicating the pattern of the wavefront modulator etched in the wafer, where the pattern of the wavefront modulator can include a multiple number of annular regions, and the resolution or focal depth of the light can be adjusted according to a diameter or a height difference of the multiple annular regions.

According to one aspect, the replicating of the pattern of the wavefront modulator etched in the wafer can include: applying polydimethylsiloxane (PDMS) over the wafer; curing the polydimethylsiloxane over the wafer; removing the polydimethylsiloxane from the wafer; applying a UV-curable epoxy over a lens; arranging the polydimethylsiloxane removed from the wafer over the UV-curable epoxy; and replicating the pattern of the wavefront modulator onto the UV-curable epoxy, where a spacer and an optical fiber can be assembled onto the lens.

According to one aspect, the replicating of the pattern of the wavefront modulator etched in the wafer can include: applying a UV-curable epoxy over the wafer; and curing the UV-curable epoxy over the wafer, where a lens, a spacer, and an optical fiber can be assembled onto the cured UV-curable epoxy.

According to one aspect, a step of applying a coating agent over the wafer. can further be included, before applying the UV-curable epoxy over the wafer.

With an optical probe and a method for manufacturing the optical probe according to one embodiment, it is possible to extend the measurement region along the depth direction while at the same time improving lateral resolution through an optimal design of the wavefront modulator.

With an optical probe and a method for manufacturing the optical probe according to one embodiment, the wavefront modulator can be provided with a multiple number of annular regions, and it is possible to improve resolution or focal depth by changing the diameter sizes or height difference between the multiple annular regions.

With an optical probe and a method for manufacturing the optical probe according to one embodiment, it is possible to conduct not only forward scanning but also circumferential scanning and 2-dimensional scanning by arranging a prism or a mirror in front of the optical probe.

An optical probe and a method for manufacturing the optical probe according to one embodiment can use a common path optical probe to enable an easy alignment of the optical system and offer a solution to the problems of artifacts and common noise resulting from dispersion.

With an optical probe and a method for manufacturing the optical probe according to one embodiment, the optical probe can be manufactured via methods such as replica molding, precision molding, and direct molding, which are types of soft lithography, to allow easy manufacture and a smaller size for the optical probe.

With an optical probe and a method for manufacturing the optical probe according to one embodiment, it is possible to conduct a precise diagnosis of lesions over a broader range compared to existing optical probes, to thus allow wide utility in diagnosing cardiovascular and digestive diseases, enable precise early diagnosis of arteriosclerosis, cancer in the digestive tract, etc., and aid in the research of pathogenic mechanisms by allowing the observation of reactions to drugs and treatments and of lesion developments, etc.

With an optical probe and a method for manufacturing the optical probe according to one embodiment, it is possible to replace only the optical probe portion of an existing imaging device, and this allows application in various fields.

BRIEF DESCRIPTION OF THE DRAWINGS

FIG. 1 illustrates an optical probe according to one embodiment.

FIGS. 2a and 2b schematically illustrate a plan view and a cross-sectional view of the wavefront modulator in an optical probe according to one embodiment.

FIG. 3 illustrates simulation results of utilizing the wavefront modulator in an optical probe according to one embodiment.

FIG. 4 illustrates the optical probe of FIG. 1 with a prism further included.

FIG. 5 illustrates the optical probe of FIG. 1 with a mirror further included.

FIG. 6 illustrates the optical probe of FIG. 1 with a splitter further included.

FIG. 7 is a flowchart illustrating a method for manufacturing an optical probe according to one embodiment.

FIGS. 8a and 8b are flowcharts that further detail the step of replicating the pattern of the wavefront modulator.

FIGS. 9a to 9f illustrate the procedures by which an optical probe according to one embodiment is manufactured.

FIGS. 10a to 10c are photographs illustrating the procedures by which a wavefront modulator is manufactured.

DETAILED DESCRIPTION OF THE INVENTION

Certain embodiments of the present invention are described below in more detail with reference to the accompanying drawings. However, the present invention is not limited by or restricted to such embodiments. In the drawings, like reference numerals are used to represent like components.

FIG. 1 illustrates an optical probe according to one embodiment, FIGS. 2a and 2b schematically illustrate a plan view and a cross-sectional view of the wavefront modulator in an optical probe according to one embodiment, FIG. 3 illustrates simulation results of utilizing the wavefront modulator in an optical probe according to one embodiment, FIG. 4 illustrates the optical probe of FIG. 1 with a prism further included, FIG. 5 illustrates the optical probe of FIG. 1 with a mirror further included, and FIG. 6 illustrates the optical probe of FIG. 1 with a splitter further included.

Referring to FIG. 1, an optical probe 10 according to one embodiment can include an optical fiber 100, a capillary 200, a spacer 300, a lens 400, and a wavefront modulator 500.

The light intended for scanning a target can be made to enter the optical fiber 100 from a light source (not shown).

The optical fiber 100 can be prepared, for example, as a single mode fiber.

Optical fibers 100 can be divided largely into the single mode fiber and the multi-mode fiber. The single mode fiber has a very small core of less than 10 μm and entails just one form of optical transmission, so that there is very little optical attenuation and virtually no alterations or distortions in the signals, and therefore allows transmission of signals over long distances.

The capillary 200 can be attached to the outer perimeter of the optical fiber 100.

The capillary 200 may be a tube having a very small diameter and can be prepared, for example, in a cylindrical shape to surround the outer perimeter of the optical fiber 100.

More specifically, the optical fiber 100 can penetrate through the capillary 200, with the optical fiber 100 extending through one end of the capillary 200 towards the inside of the capillary 200 and reaching the other end of the capillary 200, so that the optical fiber 100 may be exposed to the exterior at the other end of the capillary 200.

Here, the optical fiber 100 and the capillary 200 can be arranged on a common axis. Thus, the core of the optical fiber 100 can be arranged in the center at both ends of the capillary 200, and the end portion of the optical fiber 100 can be exposed to the exterior at the center of the other end of the capillary 200.

The manner in which the capillary 200 is coupled with the optical fiber 100 as described above is referred to as a fiber pigtail and generally can often be used in module packaging.

In this way, the capillary 200 allows easier application of the optical fiber 100 to the optical probe 10 and allows easier optical alignment not only in the optical probe 10 but also in various optical systems.

The spacer 300 can be connected to the other end of the capillary 200.

The spacer 300 can be prepared, for example, as a glass spacer.

The spacer 300 can be prepared in a cylindrical shape that extends over a certain length with one end adjoining the other end of the capillary 200 and can be arranged on a common axis with the capillary 200.

However, the spacer 300 may not include the optical fiber 100 therein but allows the light that has been transferred through the optical fiber 100 to be diffused from the end portion of the optical fiber 100.

Here, the light can be diffused within the spacer 300 to be in correspondence to the diameter of the spacer 300.

More specifically, from the center at the one end of the spacer 300 that is connected to the capillary 200, the light may be gradually diffused to be spread over the entire surface at the other end of the spacer 300.

Thus, the spacer 300 can serve both to transfer and diffuse the light provided by the optical fiber 100.

The lens 400 can be connected to the other end of the spacer 300.

The lens 400 can be prepared, for example, as a GRIN lens, where a GRIN lens is a glass that has a particular refraction gradient and is capable of functioning as a lens, GRIN being an abbreviation of 'gradient index.' Here, the refraction gradient may be achieved by an ion exchange of a glass based on diffusion or by an ion exchange of a porous gel obtained with a sol-gel process.

The lens 400 can be prepared, for example, in a cylindrical shape that extends over a certain length with one end adjoining the other end of the spacer 300 and can be arranged on a common axis with the capillary 200 and the spacer 300.

Here, the lens 400 can serve to focus the light diffused in the spacer 300. More specifically, the light that has been diffused in the spacer 300 to correspond to the diameter of the spacer 300 can be focused as it passes through the lens 400.

The wavefront modulator 500 can be connected to the other end of the lens 400.

The wavefront modulator 500 can be prepared, for example, as a binary-phase wavefront shaping filter and can shape the light entered into the optical fiber 100 to a specific form.

Referring to FIGS. 2a and 2b, the design plan for the wavefront modulator 500, particularly the design plan of the pattern formed in the wavefront modulator 500, can be provided as follows.

The wavefront modulator 500 can include a multiple number of annular regions.

While the drawings depict four annular regions, the annular regions can be prepared in various numbers of at least two or more.

The descriptions below are provided using an example in which the wavefront modulator 500 includes four annular regions.

The multiple annular regions can include a first annular region 510, second annular region 520, third annular region 530, and fourth annular region 540.

The first annular region 510 can be prepared as an annular region positioned at the center of the wavefront modulator 500, the second annular region 520 can be prepared as an annular region that is radially separated by a particular gap from the first annular region 510, the third annular region 530 can be prepared as an annular region that is arranged between the first annular region 510 and the second annular region 520, and the fourth annular region 540 can be prepared as an annular region that surrounds the outer perimeter of the second annular region 520.

Here, since the first annular region 510 may be positioned at the center of the wavefront modulator 500, the midpoint of the first annular region 510 can be positioned on the common axis with the optical fiber 100.

More specifically, the first annular region 510 can have a diameter size of a, the second annular region 520 can have a diameter size of c, the third annular region 530 can have a diameter size of b, and the fourth annular region 540 can have a diameter size corresponding to the overall diameter of the wavefront modulator 500.

Here, the diameter sizes of the first annular region 510, second annular region 520, third annular region 530, and fourth annular region 540 can be related to the type of the optical fiber 100 and to the size of the light entered into the wavefront modulator.

During the manufacture of the wavefront modulator 500, the optimal values of a, b, and c can be designed via detailed simulations.

Also, the refractive index at the first annular region 510 or the second annular region 520 can be n1, and the refractive index at the third annular region 530 or the fourth annular region 540 can be n2.

Here, a height difference of d can be formed between the first annular region 510 or second annular region 520 and the third annular region 530 or fourth annular region 540.

For example, the first annular region 510 or the second annular region 520 can be formed with a lower height than the third annular region 530 or the fourth annular region 540.

With the first annular region 510, second annular region 520, third annular region 530, and fourth annular region 540 included thus, a pattern can be formed in the wavefront modulator 500.

Also, when the light is modulated to a binary phase at the wavefront modulator 500, the refractive indexes and the height difference can have the following relationship.

$$d = \frac{\lambda}{2(n_1 - n_2)}$$

Here, d is the height difference between the multiple annular regions, n1 is the refractive index of the first annular region or second annular region, n2 is the refractive index of the third annular region or fourth annular region, and $\lambda$ is the wavelength of the light.

Thus, the height difference between adjacent annular regions from among the multiple annular regions can be adjusted according to the difference in refractive indexes between adjacent annular regions from among the multiple annular regions, the type of the optical fiber 100, and the wavelength of the light entered into the wavefront modulator.

More specifically, the light entered into the optical fiber 100 can be made to have a phase difference of $\pi$ as the light passes through the wavefront modulator 500, for example through different annular regions.

The light having such phase difference can cause interference and change the shape of the light, making it possible to extend the measurement region along the depth direction while at the same time improving the lateral resolution of the light from the optical probe 10 according to one embodiment.

Here, the lateral direction can refer to the radial direction of the wavefront modulator 500, and improving the lateral resolution can refer to the light that has passed through the wavefront modulator 500 providing a higher resolution in the lateral direction in the focal region.

Also, the depth direction can refer to the length direction of the optical fiber 100 (in other words, the direction of the optical axis) or the length direction of the optical probe 10, and extending the measurement region along the depth direction can refer to extending the length of the region in which the light that has passed through the wavefront modulator 500 is able to form a focus on the common axis of the optical fiber 100, capillary 200, spacer 300, lens 400, and wavefront modulator 500 and maintain a high resolution in the lateral direction.

For example, in order to implement a phase difference of $\pi$ between the multiple annular regions, it can be advantageous for the light passing through adjacent regions of the multiple annular regions to have an optical path difference of $\lambda/2$.

From the equation set forth above, the value of d that yields an optical path difference of $\lambda/2$ for the light can be calculated.

Although an equation representing the relationship between refractive indexes and height difference is provided above for the case in which the light is modulated to a binary phase in the wavefront modulator 500, it is to be appreciated that the light can be changed to an arbitrary phase by using an equation representing a different relationship between the refractive indexes and height difference.

Thus, by adequately designing the diameter sizes and height difference of the multiple number of annular regions, it is possible to improve the resolution and focal depth of the optical probe 10.

Conversely, the diameter sizes and height difference of the multiple number of annular regions can be determined according to the required levels of improvement in the resolution and focal depth of the optical probe 10.

For example, the pattern design for a wavefront modulator 500 capable of improving resolution by 5% and improving focal depth by 100% can be different from the pattern design for a wavefront modulator 500 capable of improving resolution by 10% and improving focal depth by 50%, and the designing of the pattern for the wavefront modulator 500 can be performed in various ways for different combinations of resolution and focal depth.

This can be predicted in advance through simulations before the manufacture of the wavefront modulator 500, with the pattern for the wavefront modulator 500 manufactured differently to be appropriate for each case.

Also, with reference to FIGS. 3a and 3b, the focal depth of the optical probe 10 can be different for cases where a wavefront modulator 500 is not applied and where a wavefront modulator 500 is applied.

To be more specific, compared to the case in which there is no wavefront modulator 500 applied to an optical probe 10 based on one embodiment, illustrated in FIG. 3a, it can be seen that the case in which there is a wavefront modulator 500 applied to the optical probe 10 according to one embodiment, as illustrated in FIG. 3b, has the focal depth improved by about 3 times.

Thus, an optical probe 10 according to one embodiment can improve lateral resolution and extend the measurement region in the depth direction through an optimal design of the wavefront modulator, whereby the forward scanning of a target can be performed in an efficient manner.

While the optical probe 10 according to one embodiment has been described that includes the capillary 200, spacer 300, lens 400, and wavefront modulator 500 in said order, it is to be appreciated that the optical probe 10 can be provided in various configurations.

For example, an optical probe 10 can have the spacer 300 omitted, have the order of the spacer 300 and lens 400 altered such that the wavefront modulator 500 is mounted on the end portion of the spacer 300, or have the wavefront modulator 500 arranged between the spacer 300 and the lens 400.

A prism 600 can be arranged in front of an optical probe 10 according to one embodiment configured as above.

Referring to FIG. 4, the prism 600 can have an inclined surface 602 formed facing the wavefront modulator 500 of the optical probe 10, and the light that has passed through the wavefront modulator 500 can be reflected off the inclined surface 602.

The light reflected from the inclined surface 602 can form a focus on an axis that is perpendicular to the common axis of the optical fiber 100, capillary 200, spacer 300, lens 400, and wavefront modulator 500.

Arranging a prism 600 in front of the optical probe 10 in this manner also makes it possible to conduct circumferential scanning.

Referring to FIG. 5, a mirror 700 can be arranged in front of, and separated from, an optical probe 10 according to one embodiment.

The mirror 700 can be prepared, for example, as a MEMS mirror, and the inclination angle of the mirror 700 can be controlled.

Based on the control of the inclination angle of the mirror 700, the direction in which the light that has passed through the wavefront modulator 500 is reflected can be controlled, and the point at which the focus of the light is formed can be controlled.

For example, the light passed through the wavefront modulator 500 can be reflected off the inclined surface of the mirror 700 and can form a focus on an axis that is perpendicular to the common axis of the optical fiber 100, capillary 200, spacer 300, lens 400, and wavefront modulator 500.

Arranging a mirror 700 in front of the optical probe 10 in this manner also makes it possible to conduct 2-dimensional scanning.

Referring to FIG. 6, a splitter 800 can be arranged in front of, and separated from, an optical probe 10 according to one embodiment.

For example, one side 802 of the splitter 800 facing the wavefront modulator 500 can be abraded to 40 to 50 degrees, for instance, and applied with a splitter coating, enabling the function of a splitter.

The other side 804 of the splitter 800 opposite the one side can be applied with a reflective coating to serve as a mirror.

Here, a portion of the light having passed through the wavefront modulator 500 can be reflected off a surface of the splitter 800, for example off the one side 802 of the splitter 800, to form a focus on an axis perpendicular to the common axis of the optical fiber 100, capillary 200, spacer 300, lens 400, and wavefront modulator 500.

On the other hand, the remaining portion of the light having passed through the wavefront modulator 500 can pass through the one side 802 of the splitter 800 to form a focus on the common axis. Here, the focus can be formed on the other side 804 of the splitter 800.

Here, using a common path optical probe 10 can allow easy alignment within the optical system and can resolve problems of common noise and artifacts resulting from dispersion.

A description is provided above of an optical probe according to one embodiment, and below, a description is provided on a method for manufacturing an optical probe according to one embodiment.

FIG. 7 is a flowchart illustrating a method for manufacturing an optical probe according to one embodiment, FIGS. 8a and 8b are flowcharts that further detail the step of replicating the pattern of the wavefront modulator, FIGS. 9a to 9f illustrate the procedures by which an optical probe according to one embodiment is manufactured, and FIGS. 10a to 10c are photographs illustrating the procedures by which a wavefront modulator is manufactured.

Referring to FIGS. 7 through 9f, an optical probe according to one embodiment can be manufactured as described in the following.

First, the pattern of the wavefront modulator for modulating the wavefront of the light entered into the optical fiber may be designed (S10).

Here, the pattern of the wavefront modulator can include a multiple number of annular regions, where the diameters or height difference of the multiple annular regions can be used to adjust the resolution or focal depth of the light.

Then, the pattern of the wavefront modulator may be etched into a wafer (S20).

Here, the multiple annular regions can be etched in the wafer via anisotropic etching.

Afterwards, the pattern of the wavefront modulator etched into the wafer may be replicated (S30).

Here, the pattern of the wavefront modulator etched in the wafer can be replicated by various methods using polymers.

For example, referring to FIG. 8a and FIGS. 9a to 9f, one method can include the steps of applying polydimethylsiloxane (PDMS) over the wafer (S31), curing the polydimethylsiloxane over the wafer (S32), removing the polydimethylsiloxane from the wafer (S33), applying a UV-curable epoxy over the lens (S34), arranging the polydimethylsiloxane removed from the wafer over the UV-curable epoxy (S35); and replicating the pattern of the wavefront modulator onto the UV-curable epoxy (S36).

Thus, the pattern of the wavefront modulator etched into the wafer can be preliminarily replicated using polydimethylsiloxane (PDMS) and afterwards secondarily replicated using UV-curable epoxy applied onto the lens.

Here, the UV-curable epoxy can be applied on the lens in a thickness of less than 10 μm, and the UV-curable epoxy applied on the lens can itself serve as the wavefront modulator.

In this case, concurrently with replicating the pattern of the wavefront modulator etched in the wafer, the replicated pattern of the wavefront modulator can be mounted onto the lens.

Therefore, it is possible to manufacture the optical probe by assembling the spacer and the optical fiber onto the lens.

Conversely, with reference to FIG. 8b, it is possible to replicate the pattern of the wavefront modulator in a way that entails mounting the wavefront modulator onto the lens after manufacturing the wavefront modulator separately.

More specifically, the wavefront modulator can be manufactured by applying the UV-curable epoxy over the wafer (S37) and curing the UV-curable epoxy on the wafer (S38).

Also, a step of applying a coating agent over the wafer can further be included before the UV-curable epoxy is applied over the wafer, and after a slippery coating such as a Teflon coating, etc., is applied on the wafer, the UV-curable epoxy can be cured for the manufacture of the wavefront modulator.

Onto a wavefront modulator thus manufactured, the lens, spacer, and optical fiber can be assembled to manufacture the optical probe.

As described above, the wavefront modulator can be manufactured in various ways, and therefore an optical probe according to one embodiment can also be manufactured in various ways.

By referring to FIGS. 10a to 10c, one can observe the pattern of the wavefront modulator on the wafer, polydimethylsiloxane, and lens.

Referring to FIG. 10a, the pattern of the wavefront modulator on the wafer can be formed including a multiple number of annular regions; referring to FIG. 10b, the pattern of the wavefront modulator can be replicated onto the polydimethylsiloxane applied over the wafer; and referring to FIG. 10c, the pattern of the wavefront modulator can be replicated onto the UV-curable epoxy applied over the lens.

Thus, it can be observed that the wavefront modulator has been manufactured in excellent quality.

As the method for manufacturing an optical probe according to one embodiment allows manufacture by way of replica molding, which is a form of soft lithography, it is possible to manufacture the optical probe easily and in a small size.

Although the method for manufacturing an optical probe according to one embodiment has been described using an example in which the manufacture utilizes one type of soft lithography, i.e. replica molding, it is to be appreciated that the manufacture can utilize other methods, such as for example precision molding and direct writing methods.

Furthermore, an optical probe manufactured by a method for manufacturing an optical probe according to one embodiment can diagnose lesions with precision over a broader range compared to existing optical probes, to thus allow wide utility in diagnosing cardiovascular and digestive diseases, can provide precise early diagnosis of arteriosclerosis, cancer in the digestive tract, etc., can aid in the research of pathogenic mechanisms by allowing the observation of reactions to drugs and treatments and of lesion developments, etc., and also can replace just the optical probe portion of an existing imaging device to thus allow application in various fields.

While the spirit of the invention has been described in detail with reference to particular embodiments, the embodiments are for illustrative purposes only and do not limit the invention. It is to be appreciated that those skilled in the art can change or modify the embodiments without departing from the scope and spirit of the invention. Thus, the spirit of the present invention is not to be confined to the embodiments described above but rather encompasses all equivalents and variations.

What is claimed is:

1. An optical probe comprising:
    an optical fiber configured to carry light for scanning a target, the light entering from a light source;
    a lens configured to focus the light exiting the optical fiber; and
    a wavefront modulator having a pattern formed therein, the pattern configured to modulate a wavefront of the light exiting the lens,
    wherein the optical fiber, the lens, and the wavefront modulator are arranged along a common axis,
    wherein the light exiting the wavefront modulator forms a focus on the common axis, and a resolution or a focal depth of the light exiting the wavefront modulator is adjusted according to a design of the pattern formed in the wavefront modulator,
    wherein the pattern formed in the wavefront modulator comprises a plurality of annular regions, the plurality of annular regions comprising:
        a first annular region; and
        a second annular region radially separated from the first annular region, and
    wherein a height of the first annular region is different from a height of the second annular region such that a height difference between the plurality of annular regions satisfies an equation:

$$d = \frac{\lambda}{2(n_1 - n_2)}$$

where d is the height difference between the plurality of annular regions,
n1 is a refractive index of the first annular region,
n2 is a refractive index of the second annular region, and
λ is the wavelength of the light.

2. The optical probe of claim 1, wherein
    the plurality of annular regions further comprise a third annular region,
    the second annular region is arranged between the first annular region and the third annular region, and
    the resolution or the focal depth of the light exiting the wavefront modulator is adjustable by the height difference or a diameter size of the first annular region, the second annular region, and the third annular region.

3. The optical probe of claim 2, wherein the first annular region is positioned on the common axis, and
    the light having passed through the first annular region, the second annular region, and the third annular region forms a focus on the common axis.

4. The optical probe of claim 1, further comprising:
    a prism configured to refract light exiting the wavefront modulator, the prism separated from the wavefront modulator such that the light exiting the prism forms a focus on an axis perpendicular to the common axis.

5. The optical probe of claim 1, further comprising:
a mirror separated from and arranged in front of the wavefront modulator and configured to reflect the light exiting the wavefront modulator,
wherein a point at which the light exiting the wavefront modulator forms a focus is controllable by a control of an inclination angle of the mirror.

6. The optical probe of claim 1, further comprising:
a splitter separated from the wavefront modulator,
wherein a portion of the light exiting the wavefront modulator is reflected off a surface of the splitter to form a focus on an axis perpendicular to the common axis, and
a remaining portion of the light exiting the wavefront modulator passes through a surface of the splitter to form a focus on the common axis.

7. The optical probe of claim 6, wherein one side of the splitter facing the wavefront modulator is abraded to an angle of 40 to 50 degrees and applied with a splitter coating, and
an opposite side of the splitter is applied with a reflective coating.

8. The optical probe of claim 1, further comprising:
a spacer configured to diffuse light exiting the optical fiber such that the light exiting the optical fiber is diffused to correspond to a diameter of the spacer.

\* \* \* \* \*